US012808855B2

(12) United States Patent
Xu et al.

(10) Patent No.: US 12,808,855 B2
(45) Date of Patent: Nov. 24, 2026

(54) FLOW CALIBRATION DEVICE FOR GAS MONITORING SYSTEM

(71) Applicant: LIFE SAFETY DISTRIBUTION GMBH., Rolle (CH)

(72) Inventors: Hui Xu, Charlotte, NC (US); Zuohua Li, Charlotte, NC (US); Liangliang Ma, Charlotte, NC (US); Bo Chen, Charlotte, NC (US)

(73) Assignee: LIFE SAFETY DISTRIBUTION GMBH., Rolle (CH)

( * ) Notice: Subject to any disclaimer, the term of this patent is extended or adjusted under 35 U.S.C. 154(b) by 274 days.

(21) Appl. No.: 18/778,468

(22) Filed: Jul. 19, 2024

(65) Prior Publication Data

US 2025/0035604 A1 Jan. 30, 2025

(30) Foreign Application Priority Data

Jul. 26, 2023 (CN) ........................ 202310930173.2

(51) Int. Cl.
*G01N 33/00* (2006.01)
*G01F 25/10* (2022.01)

(52) U.S. Cl.
CPC ........... *G01N 33/007* (2013.01); *G01F 25/10* (2022.01); *G01N 33/0006* (2013.01)

(58) Field of Classification Search
CPC ... G01N 33/007; G01N 33/0006; G01F 25/10
See application file for complete search history.

(56) References Cited

U.S. PATENT DOCUMENTS

| | | | | |
|---|---|---|---|---|
| 6,997,347 | B2 | 2/2006 | Peng et al. | |
| 7,146,841 | B2 * | 12/2006 | Forrest | G01N 33/0006 73/1.06 |
| 10,890,475 | B2 * | 1/2021 | Shakudo | G01F 1/88 |
| 11,392,148 | B2 * | 7/2022 | Nguyen | G01F 1/68 |
| 12,078,566 | B2 * | 9/2024 | Xu | G01L 19/14 |
| 2006/0212233 | A1 * | 9/2006 | Wong | G01F 25/15 702/50 |
| 2020/0124503 | A1 * | 4/2020 | Yamaguchi | G01N 1/2273 |
| 2024/0401497 | A1 * | 12/2024 | Al Rashed | F01D 21/003 |
| 2025/0370485 | A1 * | 12/2025 | Tokunaga | G01F 1/363 |

FOREIGN PATENT DOCUMENTS

| | | |
|---|---|---|
| CN | 206248631 U | 6/2017 |
| CN | 113484466 A | 10/2021 |

* cited by examiner

*Primary Examiner* — Ryan D Walsh
(74) *Attorney, Agent, or Firm* — Alston & Bird LLP

(57) ABSTRACT

A flow calibration device and method for a gas monitoring system. The flow calibration device includes, but not limited to: an inlet configured to facilitate an inflow of a gas flow sample from a nose grip of the gas monitoring system; an outlet configured to facilitate an outflow of the gas flow sample to a port manifold of the gas monitoring system; a flow channel defined between the inlet and the outlet; a pressure transducer, configured to calibrate at least one sample pressure transducer of the gas monitoring system; and a valve positioned between the inlet and the outlet, configured to adjust the flow rate of the gas flow sample between a first benchmark flow rate and a second benchmark flow rate.

20 Claims, 6 Drawing Sheets

FLOW CALIBRATION DEVICE FOR GAS MONITORING SYSTEM

CROSS-REFERENCE TO RELATED APPLICATIONS

This application claims priority pursuant to 35 U.S.C. 119(a) to Chinese Application No. 202310930173.2, filed Jul. 26, 2023, which application is incorporated herein by reference in its entirety.

FIELD OF THE INVENTION

Exemplary embodiments of the present disclosure relate generally to flow calibration devices for gas monitoring systems, and more particularly, in some examples, to devices and methods for calibrating gas monitoring systems.

BACKGROUND

Applicant has identified many technical challenges and difficulties associated with calibrating gas monitoring system. Through applied effort, ingenuity, and innovation, Applicant has solved problems relating to expediting the calibration process by developing solutions embodied in the present disclosure, which are described in detail below.

BRIEF SUMMARY

Various embodiments described herein relate to components, apparatuses, and systems for measuring a fluid turbidity and a fluid composition.

In accordance with various embodiments of the present disclosure, a flow calibration device for a gas monitoring system is provided. The flow calibration device includes, but not limited to: an inlet configured to facilitate an inflow of a gas flow sample from a nose grip of the gas monitoring system; an outlet configured to facilitate an outflow of the gas flow sample to a port manifold of the gas monitoring system; a flow channel defined between the inlet and the outlet; a pressure transducer, configured to calibrate at least one sample pressure transducer of the gas monitoring system; and a valve positioned between the inlet and the outlet, configured to adjust a flow rate of the gas flow sample between a first benchmark flow rate and a second benchmark flow rate.

In some embodiments, the valve is a needle valve configured to adjust the flow rate of the gas flow sample.

In some embodiments, the flow calibration device further includes a resistor inserted in the flow channel to restrict the flow rate of the gas flow sample.

In some embodiments, the flow calibration device further includes a first terminal positioned upstream of the resistor and a second terminal positioned downstream of the resistor, and the pressure transducer is configured to measure the flow rate of the gas flow sample by monitoring a pressure difference across the first terminal and the second terminal.

In some embodiments, the nose grip comprises a by-pass mechanism configured to divert the gas flow sample from the gas monitoring system to the inlet of the flow calibration device, and the inlet is configured to facilitate the inflow of the gas flow sample from the nose grip of the gas monitoring system.

In some embodiments, the by-pass mechanism is a Tee valve.

In some embodiments, the outlet is configured to facilitate the outflow of the gas flow sample to the port manifold of the gas monitoring system.

In some embodiments, the at least one sample pressure transducer is configured to measure the flow rate of the gas flow sample.

In some embodiments, the pressure transducer is configured to measure the flow rate of the gas flow sample.

In some embodiments, calibrating the at least one sample pressure transducer includes: controlling the flow rate of the gas flow sample to be at a first benchmark flow rate by adjusting the valve; calibrating the at least one sample pressure transducer based on the first benchmark flow rate; controlling the flow rate of the gas flow sample to be at a second benchmark flow rate by adjusting the valve; and calibrating the at least one sample pressure transducer based on the second benchmark flow rate.

In some embodiments, the first benchmark flow rate is 200 cc/min, and the second benchmark flow rate is 0 cc/min.

In some embodiments, the gas monitoring system further comprises an optical block and a media positioned between the optical block and the nose grip, and the optical block is configured to collect data by sensing a change in the media that is exposed to the gas flow sample.

In some embodiments, the gas monitoring system further comprises a controller component electrically coupled to the optical block, configured to determine a concentration of the gas flow sample based on the data collected on the optical block.

In some embodiments, the media is a chemcassette tape that changes color in an instance in which the chemcassette is exposed to the gas flow sample.

According to another embodiment, a method for calibrating a gas monitoring system by a controller component is provided. The method includes, but not limited to: facilitating an inflow of a gas flow sample from a nose grip of the gas monitoring system to an inlet of a flow calibration device; facilitating an outflow of the gas flow sample from an outlet of the flow calibration device to a port manifold of the gas monitoring system; controlling a flow rate of the gas flow sample to be at a first benchmark flow rate by adjusting a valve of the flow calibration device; calibrating at least one sample pressure transducer of the gas monitoring system based on the first benchmark flow rate; controlling the flow rate of the gas flow sample to be at a second benchmark flow rate by adjusting the valve of the flow calibration device; and calibrating the at least one sample pressure transducer of the gas monitoring system based on the second benchmark flow rate.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
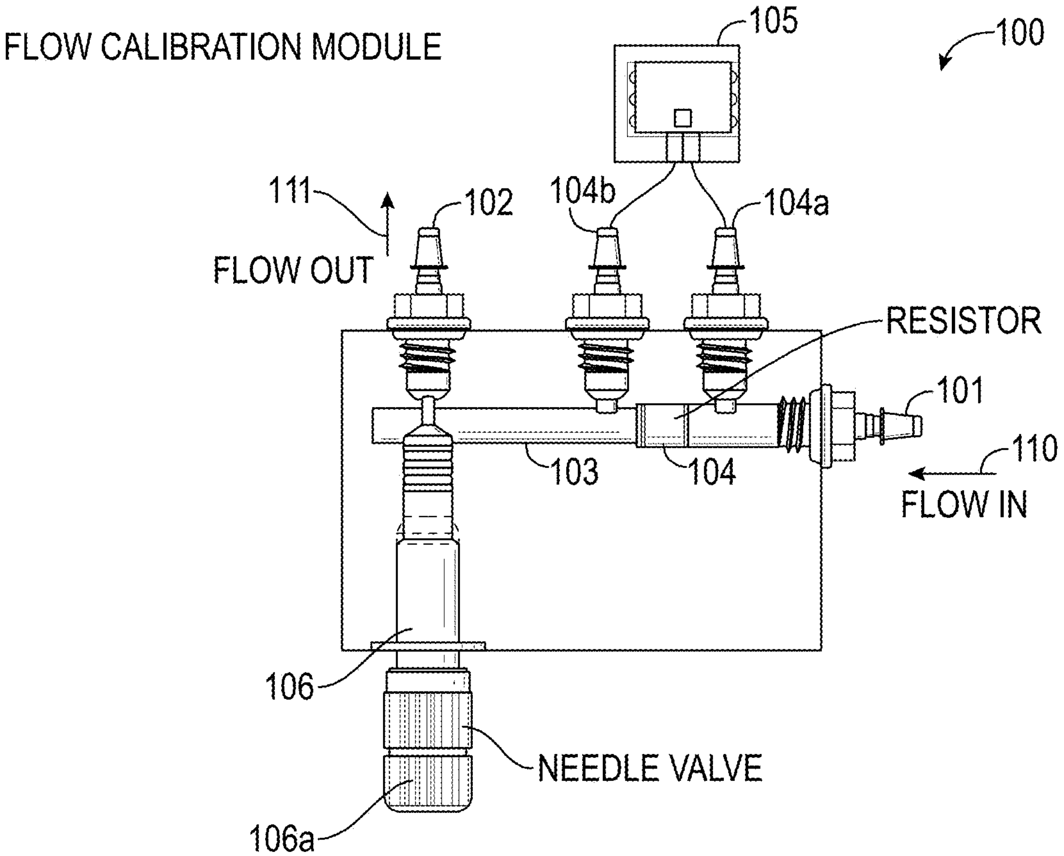
FIG. 1 illustrates an exemplary diagram depicting an example flow calibration device for a gas monitoring system, in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as "comprises", "includes", and "having" should be understood to provide support for narrower terms such as "consisting of", "consisting essentially of", and "comprised substantially of".

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

Various example embodiments address exemplary technical problems associated with calibrating a gas monitoring system. As understood by those of skill in the field to which the present disclosure pertains, for example, a gas monitoring system may be calibrated with additional or otherwise external apparatuses. For example, the additional apparatuses may comprise a pump, a vacuum meter, a flow meter, a valve, and the like. In some examples, the pump, the flow meter and the valve may control and/or measure a flow rate of a gas flow sample, such that the gas monitoring system can be calibrated with the flow meter. However, in some examples, the additional apparatuses, such as the vacuum pump, the vacuum meter, and the flow meter may be bulky, which makes them challenging to maneuver and set up with the gas monitoring system.

To address at least these exemplary problems as well as others, example apparatuses, systems, and methods described herein improve, in some examples, the calibration of a gas monitoring system by using a flow calibration device. For example, the flow calibration device for the gas monitoring system may comprise an inlet configured to facilitate an inflow of a gas flow sample from a nose grip of the gas monitoring system and an outlet configured to facilitate an outflow of the gas flow sample to a port manifold of the gas monitoring system. In some examples, the flow calibration device may further comprise a pressure transducer, configured to measure a flow rate of the gas flow sample and a valve positioned between the inlet and the outlet, configured to adjust the flow rate of the gas flow sample. In some examples, the pressure transducer may be configured to calibrate at least one sample pressure transducer of the gas monitoring system.

Referring now to FIG. 1, an example diagram illustrating an example flow calibration device 100 for a gas monitoring system in accordance with some example embodiments described herein is provided. As shown in FIG. 1, the example flow calibration device 100 may comprise an inlet 101, an outlet 102, and a flow channel 103 defined between the inlet 101 and the outlet 102.

In some embodiments, the inlet 101 may be configured to facilitate an inflow 110 of a gas flow sample from the gas monitoring system (not shown). In some examples, the inlet 101 may be configured to facilitate the inflow 110 of the gas flow sample from a nose grip (not shown) of the gas monitoring system. Further details of the nose grip of the gas monitoring system are described in reference to FIG. 4.

In some embodiments, the outlet 102 may be configured to facilitate an outflow 111 of the gas flow sample back to the gas monitoring system. In some examples, the outlet 102 may be configured to facilitate an outflow 111 of the gas flow sample back to a port manifold (not shown) of the gas monitoring system. Further details of the port manifold of the gas monitoring system are described in reference to FIG. 4.

In some embodiments, the flow channel 103 may be a cylindrical passage defined between the inlet 101 and outlet 102. Alternatively, the flow channel 103 may take a form of other shapes. In some examples, the inflow 110 of the gas flow sample may pass the flow channel 103 and exit the flow calibration device 100 via the outlet 102 to facilitate the outflow 111 of the gas flow sample.

In some embodiments, as shown in FIG. 1, the example flow calibration device 100 may further comprise a resistor

104 positioned in the flow channel 103. In some examples, the resistor 104 may be an inline flow restrictor. For example, the resistor 104 may be inserted in the flow channel 103 to restrict the flow of the gas flow sample in the flow channel 103.

In some embodiments, the example flow calibration device 100 may further comprise a pressure transducer 105. In some examples, example flow calibration device 100 may comprise a first terminal 104*a* positioned upstream of the resistor 104 and a second terminal 104*b* positioned downstream of the resistor 104. For example, the pressure transducer 105 maybe connected between the first terminal 104*a* and the second terminal 104*b*. In some examples, the pressure transducer 105 may be configured to measure a flow rate of the gas flow sample in the flow channel 103. In some examples, the pressure transducer 105 may be configured to measure the flow rate of the gas flow sample in the flow channel 103 by monitoring a pressure difference across the first terminal 104*a* and the second terminal 104*b*.

In some examples, the pressure transducer 105 may be electrically connected and/or coupled with a controller component (not shown), and the controller component may be configured to determine the flow rate of the gas flow sample.

In some embodiments, the example flow calibration device 100 may further comprise a valve 106 positioned between the inlet 101 and the outlet 102. In some examples, the valve 106 may be configured to adjust the flow rate of gas flow sample in the flow channel 103. In some examples, the valve 106 may be a needle valve. For example, the valve 106 may include a controlling element 106*a* to adjust the flow rate of the gas flow sample in the flow channel 103. For example, the controlling element 106*a* may be a turning knob, which controls a passageway (not shown) of the valve 106 by adjust the position of a needle 106*b* of the valve 106, such that the flow rate of the gas flow sample in the flow channel 103 may be precisely controlled.

Figure 2:
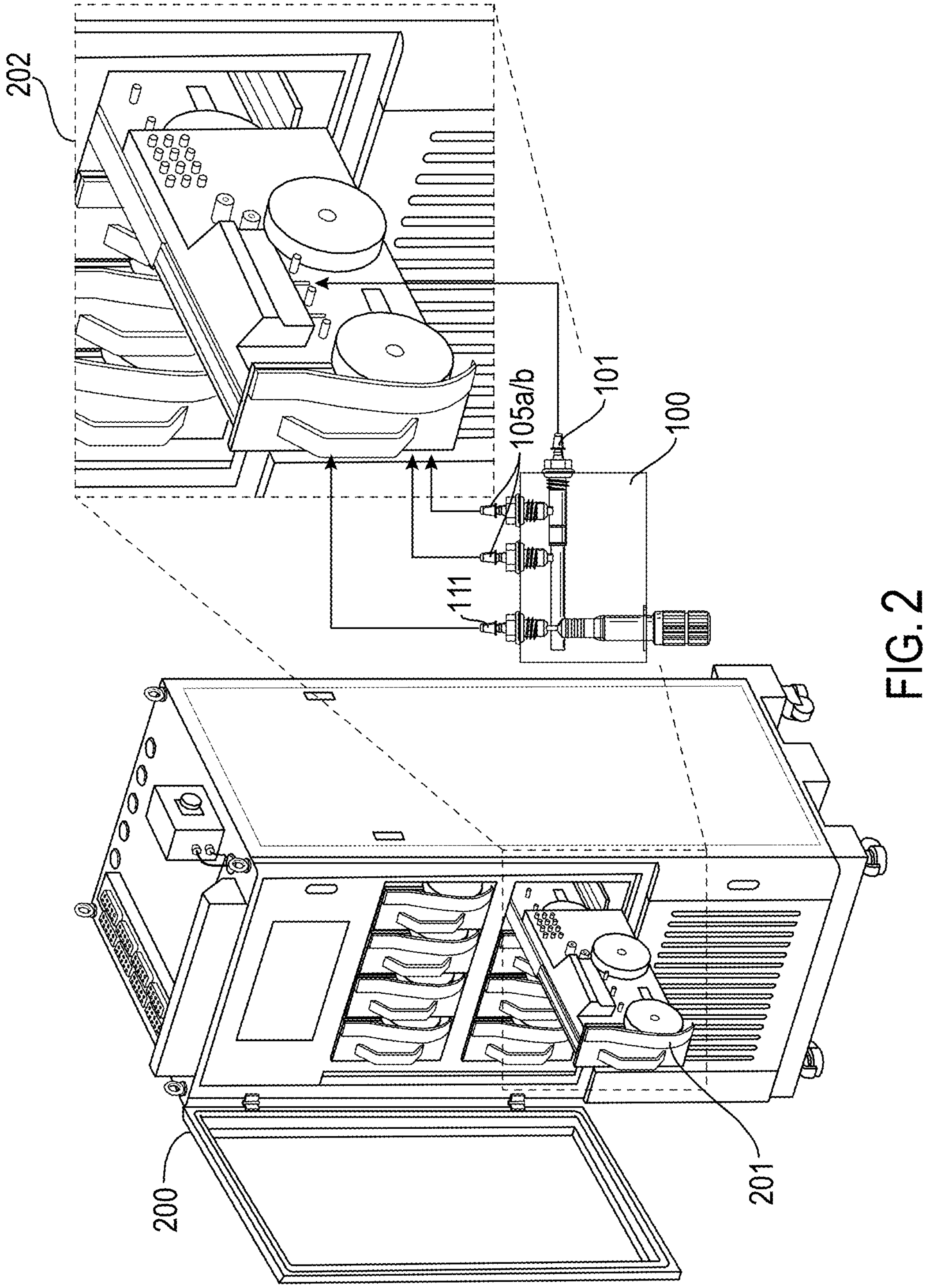
FIG. 2 illustrates an exemplary diagram depicting an example flow calibration device integrated with a gas monitoring system, in accordance with various embodiments of the present disclosure.

Referring now to FIG. 2, an example diagram illustrating an example flow calibration device 100 integrated with a gas monitoring system 200 in accordance with some example embodiments described herein is provided.

As shown in FIG. 2, the gas monitoring system 200 may receive one or more gas flow samples from one or more sampling sources and may comprise at least one analyzer module 201 that generate data associated with the sampling sources. Examples of at least one analyzer module 201 may include, but not limited to, Chemcassette® modules, and/or other modules that provide physical evidence of a gas event. Such an analyzer module may comprise mechanical and electronic components that are configured to react or process certain gases, and generate sample data. In some examples, the gas monitoring system 200 may be a multi-point gas monitoring system configured to have more than one analyzer module. In some examples, each of the at least one analyzer module 201 may have at least one detection points for the gas flow samples.

In some embodiments, the example flow calibration device 100 may be integrated with the gas monitoring system 200 by connecting with the at least one analyzer module 201. For example, as shown in a close-up view 202 of the at least one analyzer module 201, the inlet 101 may be connected with a nose grip (not shown) of the at least one analyzer module 201 and the outlet 102 may be connected to the port manifold (not shown) of the at least one analyzer module 201, such that the example flow calibration device 100 may provide a bypass for a flow passageway between the nose grip and the port manifold.

In some embodiments, the pressure transducer 105 (not shown) may be positioned and/or integrated on the at least one analyzer module 201. In some examples, the first/second terminals 104*a/b* are electrically connected and/or coupled with the pressure transducer 105. In some examples, the pressure transducer 105 may be configured to monitor a pressure difference across the first/second terminals 104*a/b*. Further details of the pressure transducer 105 are described in reference to FIG. 3.

Figure 3:
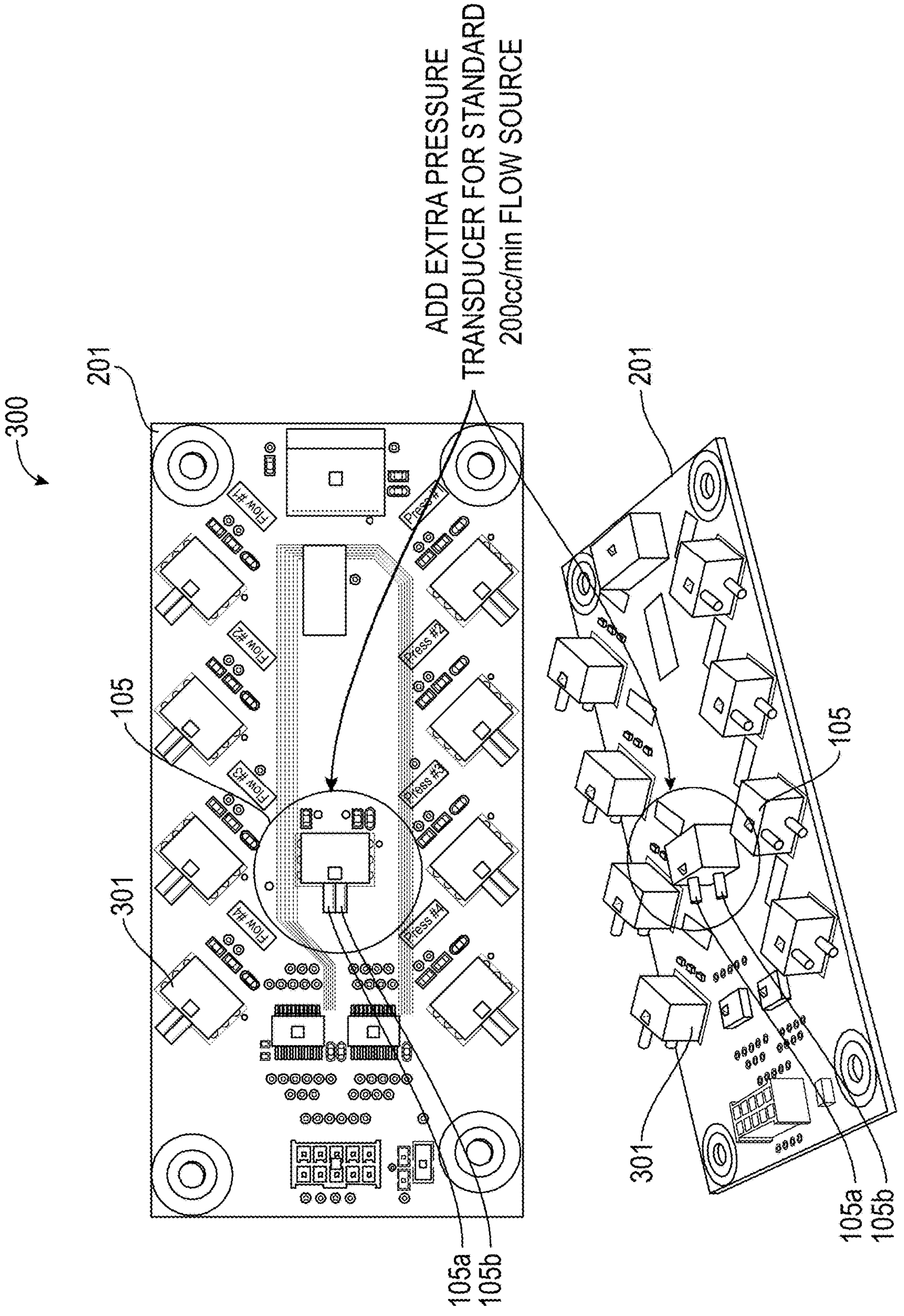
FIG. 3 illustrates an exemplary diagram depicting an example pressure transducer integrated with the at least one analyzer module, in accordance with various embodiments of the present disclosure.

Referring now to FIG. 3, an example diagram 300 illustrating an example pressure transducer 105 integrated with the at least one analyzer module 201 in accordance with some example embodiments described herein is provided. On the top of FIG. 3, an orthographic view of the at least one analyzer module 201 is provided. On the bottom of the FIG. 3, a perspective view of the at least one analyzer module 201 is provided.

In some embodiments, the example pressure transducer 105 may be positioned and/or integrated on the at least one analyzer module 201. In some examples, the pressure transducer 105 may comprise a first terminal 105*a* and a second terminal 105*b*. For example, the first terminal 105*a* of the pressure transducer 105 may be electrically connected and/or coupled with the first terminal 104*a* of example flow calibration device 100. For example, the second terminal 105*b* of the pressure transducer 105 may be electrically connected and/or coupled with the first terminal 104*a* of example flow calibration device 100.

In some examples, the pressure transducer 105 may be configured to measure the flow rate of the gas flow sample in the flow channel 103 by monitoring a pressure difference across the first terminal 104*a* and the second terminal 104*b*.

In some embodiments, the at least one analyzer module 201 may comprise at least one sample pressure transducer 301. For example, the at least one sample pressure transducer 301 may be configured to measure a flow rate of the gas flow sample in the gas monitoring system 200.

Figure 4:
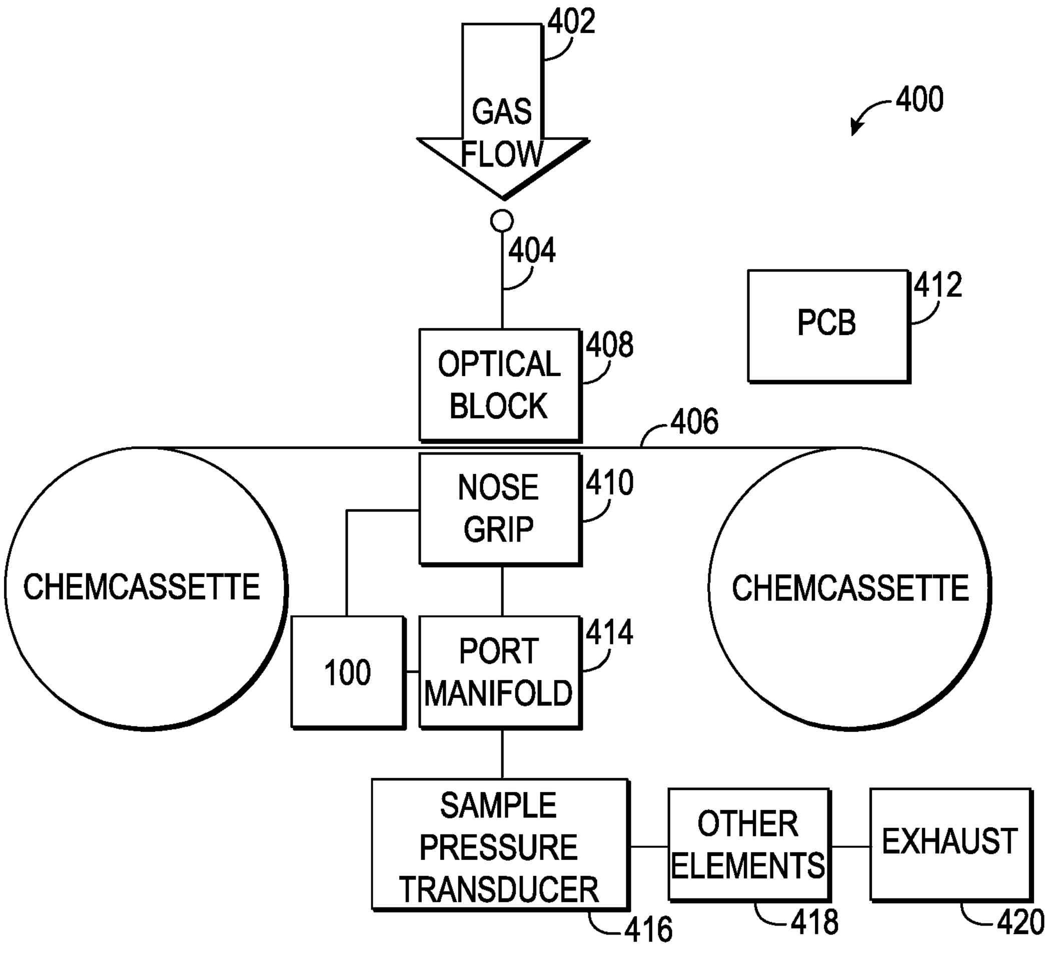
FIG. 4 illustrates an exemplary diagram depicting a block diagram depicting a flow of a gas flow sample in a gas monitoring system, in accordance with various embodiments of the present disclosure.

Referring now to FIG. 4, an example diagram illustrating a block diagram depicting a flow of a gas flow sample in a gas monitoring system 400 with the flow calibration device 100, in accordance with an example embodiment described herein.

As shown in FIG. 4, a gas flow sample 402 including one or more target gases, may inflow to a sample tubing 404 of the gas monitoring system 400.

In some embodiments, as the gas flow sample 402 inflows into the sample tubing 404 of the gas monitoring system 400, a media 406 may get exposed to the gas flow sample 402.

In some examples, the media 406 may be a chemcassette tape. For example, the chemcassette tape may operate like a ‘color changing indicator’ that changes its color upon being exposed to a target gas present in the gas flow sample 402. For example, the color of the chemcassette tape changes because of a chemical reaction between a coating of the chemcassette tape and the target gas present in the gas flow sample 402. In some examples, the chemcassette tape may be selected based on a type of the target gas to be detected or monitored by the gas monitoring system 400.

In some examples, the gas monitoring system 400 may further include an optical block 408 and a nose grip 410. In some examples, the media 406 may be supported by the nose grip and be positioned so that a surface of the media 406 is exposed to the optical block 408. For example, the optical block 408 may include an optical source and an optical sensor (not shown). In some examples, the optical block 408 may be electrically connected and/or coupled to a controller component 412 (e.g., a printed circuit board (PCB)) that controls the operations performed by the optical block 408. For example, the optical block 408 may be configured to collect data by sensing a change in the color of the media 406, in an instance, when the media 406 is being exposed to the gas flow sample 402. In some examples, a concentration of the target gas may be determined by the controller component 412 based on the data collected by the optical block 408.

In some embodiments, the gas flow sample may further flow into a port manifold 414 after the nose grip 410.

In some examples, the gas monitoring system 400 may further comprise at least one sample pressure transducer 416 configured to monitor a pressure difference across one or more sections of the gas monitoring system 400. In some examples, the at least one sample pressure transducer 416 may be electrically connected and/or coupled with the controller component 412 that determines the flow rate based on the at least one sample pressure transducer 416. For example, the controller component 412 may determine the flow rate based on the pressure difference across one or more sections of the gas monitoring system 400. In some examples, the at least one sample pressure transducer 416 described herein may correspond to the at least one sample pressure transducer 301 as described in FIG. 3.

In some examples, the gas flow sample 402 may further flow through other elements 418 of the gas monitoring system 400. For example, the other elements 418 may comprise a pump to control the flow rate of the gas flow sample 402 in the gas monitoring system 400.

In some examples, upon the measurement of a concentration of the target gas by the gas monitoring system 400, the gas flow sample 402 may get exhausted out from an exhaust port 420 of the gas monitoring system 400.

In some embodiments, the nose grip 410 may comprise a by-pass mechanism (e.g., a Tee valve) that is configured to be mechanically engaged with the example flow calibration device 100 to facilitate the gas flow sample 402 to flow to the example flow calibration device 100 or be mechanically engaged with the port manifold 414 to facilitate the gas flow sample 402 to flow to the port manifold 414. For example, the by-pass mechanism may divert the gas flow sample 402 from the gas monitoring system 400 to the inlet 101 of the flow calibration device 100.

In some examples, in an instance in which the nose grip 410 is mechanically engaged with the example flow calibration device 100, the gas flow sample 402 may flow through the example flow calibration device 100 to the port manifold 414, such that the example flow calibration device 100 may be used to perform a calibration process on the at least one sample pressure transducer 416 of the gas monitoring system 400.

For example, as shown in FIG. 1, the inlet 101 may be configured to engage with the nose grip 410, such that the gas flow sample 402 may be directed to the example flow calibration device 100. For example, the outlet 102 may be configured to engage with the port manifold 414, such that the gas flow sample 402 may flow back to the gas monitoring system 400.

In some examples, the pressure transducer 105 may be configured to calibrate the at least one sample pressure transducer 416. For example, a calibration card may be inserted between the optical block 408 and the nose grip 410 to replace the media 406 during the calibration process. For example, the calibration card may have a same impact on the flow rate of the gas flow sample 402 as the media 406. Replacing the media 406 with the calibration card may prevent waste of the media 406 during the calibration process.

In some examples, the pressure transducer 105 may be electrically connected and/or coupled with the controller component 412 and the controller component 412 may be configured to determine the flow rate of the gas flow sample 402 according to the pressure transducer 105.

In some examples, as shown in FIG. 1, the valve 106 may be adjusted to control the flow rate of the gas flow sample 402. For example, the flow rate of the gas flow sample 402 may be controlled to be a first benchmark flow rate. For example, the first benchmark flow rate may be 200 cc/min.

In some examples, the at least one sample pressure transducer 416 of the gas monitoring system 400 may be calibrated based on the first benchmark flow rate. For example, the controller component 412 may determine a first test flow rate based on the at least one sample pressure transducer 416 of the gas monitoring system 400. For example, if a magnitude of the first test flow rate is higher or lower than a magnitude of the first benchmark flow rate, the at least one sample pressure transducer 416 of the gas monitoring system 400 may be calibrated, such that the magnitude of the first test flow rate may equal to the magnitude of the first benchmark flow rate.

For example, the flow rate of the gas flow sample 402 may be controlled to be a second benchmark flow rate. For example, the first benchmark flow rate may be 0 cc/min.

In some examples, the at least one sample pressure transducer 416 of the gas monitoring system 400 may be calibrated based on the second benchmark flow rate. For example, the controller component 412 may determine a second test flow rate based on the at least one sample pressure transducer 416 of the gas monitoring system 400. For example, if a magnitude of the second test flow rate is higher or lower than a magnitude of the second benchmark flow rate, the at least one sample pressure transducer 416 of the gas monitoring system 400 may be calibrated, such that the magnitude of the second test flow rate may equal to the magnitude of the second benchmark flow rate.

Figure 5:
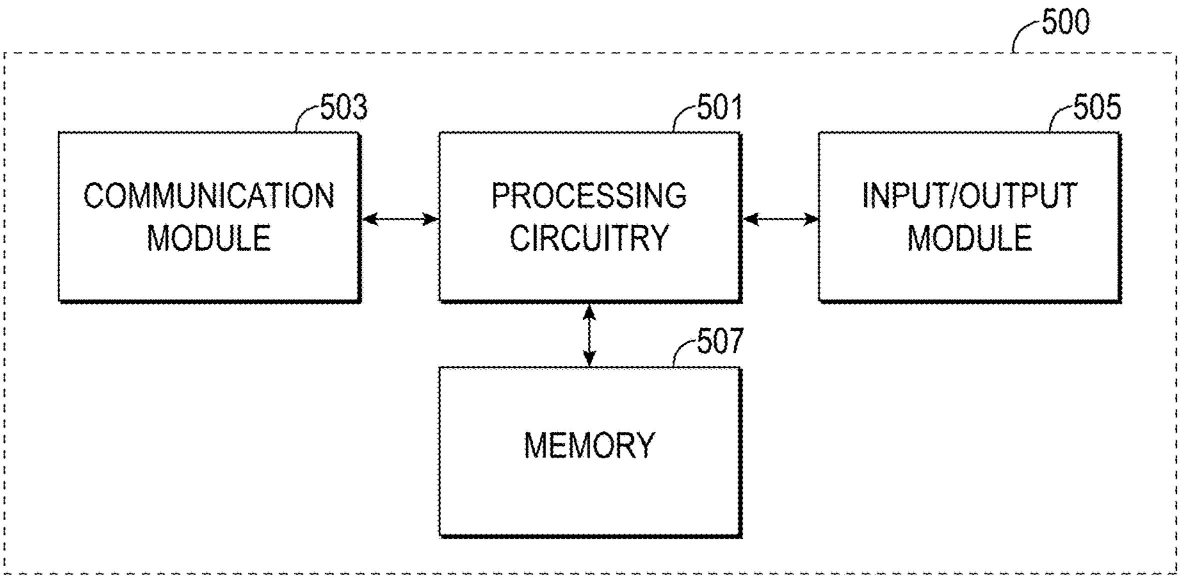
FIG. 5 illustrates an exemplary diagram depicting a controller component, in accordance with various embodiments of the present disclosure.

Referring now to FIG. 5, a schematic diagram depicting a controller component 500 in accordance with various embodiments of the present disclosure is provided. As shown, the controller component 500 may comprise a processing circuitry 501, a communication module 503, input/output module 505, a memory 507, and/or other components configured to perform various operations, procedures, functions or the like described herein. In some examples, the controller component 500 described herein may correspond to the controller component 412 as described in FIG. 4.

As shown in FIG. 5, the controller component 500 (such as the processing circuitry 501, communication module 503, input/output module 505 and memory 507) may be electrically coupled to and/or in electronic communication with the example flow calibration device 100, the at least one sample pressure transducer 416, the optical block 408, and other elements of the gas monitoring system 400. As depicted, the example flow calibration device 100, the at least one sample pressure transducer 416, the optical block 408, and other elements of the gas monitoring system 400 may exchange (e.g., transmit and receive) data with the processing circuitry 501 of the controller component 500. For example, the example flow calibration device 100, the at least one sample pressure transducer 416, the optical block 408, and other elements of the gas monitoring system 400 may generate data and transmit the data to the processing circuitry 501.

The processing circuitry 501 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). In some embodiments, the processing circuitry 501 may include one or more processors. In one exemplary embodiment, the processing circuitry 501 may be configured to execute instructions stored in the memory 507 or otherwise accessible by the processing circuitry 501. When executed by the processing circuitry 501, these instructions may enable the controller component 500 to execute one or a plurality of the functions as described herein. No matter whether it is configured by hardware, firmware/software methods, or a combination thereof, the processing circuitry 501 may include entities capable of executing operations according to the embodiments of the present invention when correspondingly configured. Therefore, for example, when the processing circuitry 501 is implemented as an ASIC, an FPGA, or the like, the processing circuitry 501 may include specially configured hardware for implementing one or a plurality of operations described herein. Alternatively, as another example, when the processing circuitry 501 is implemented as an actuator of instructions (such as those that may be stored in the memory 507), the instructions may specifically configure the processing circuitry 501 to execute one or a plurality of algorithms and operations described herein.

The memory 507 may include, for example, a volatile memory, a non-volatile memory, or a certain combination thereof. Although illustrated as a single memory in FIG. 5, the memory 507 may include a plurality of memory components. In various embodiments, the memory 507 may include, for example, a hard disk drive, a random-access memory, a cache memory, a flash memory, a Compact Disc Read-Only Memory (CD-ROM), a Digital Versatile Disk Read-Only Memory (DVD-ROM), an optical disk, a circuit configured to store information, or a certain combination thereof. The memory 507 may be configured to store information, data, application programs, instructions, and etc., so that the controller component 500 can execute various functions according to the embodiments of the present disclosure. For example, in at least some embodiments, the memory 507 may be configured to cache input data for processing by the processing circuitry 501. Additionally, or alternatively, in at least some embodiments, the memory 507 may be configured to store program instructions for execution by the processing circuitry 501. The memory 507 may store information in the form of static and/or dynamic information. When the functions are executed, the stored information may be stored and/or used by the controller component 500.

The communication module 503 may be implemented as any apparatus included in a circuit, hardware, a computer program product, or a combination thereof, which is configured to receive and/or transmit data from/to another component or apparatus. The computer program product includes computer-readable program instructions stored on a computer-readable medium (for example, the memory 507) and executed by a controller component 500 (for example, the processing circuitry 501). In some embodiments, the communication module 503 (as with other components discussed herein) may be at least partially implemented as the processing circuitry 501 or otherwise controlled by the processing circuitry 501. In this regard, the communication module 503 may communicate with the processing circuitry 501, for example, through a bus. The communication module 503 may include, for example, antennas, transmitters, receivers, transceivers, network interface cards and/or supporting hardware and/or firmware/software, and is used for establishing communication with another apparatus. The communication module 503 may be configured to receive and/or transmit any data that may be stored by the memory 507 by using any protocol that can be used for communication between apparatuses. The communication module 503 may additionally or alternatively communicate with the memory 507, the input/output module 505 and/or any other component of the controller component 500, for example, through a bus.

In some embodiments, the controller component 500 may include an input/output module 505. The input/output module 505 may communicate with the processing circuitry 501 to receive instructions input by the user and/or to provide audible, visual, mechanical, or other outputs to the user. Therefore, the input/output module 505 may include supporting devices, such as a keyboard, a mouse, a display, a touch screen display, and/or other input/output mechanisms. Alternatively, at least some aspects of the input/output module 505 may be implemented on a device used by the user to communicate with the controller component 500. The input/output module 505 may communicate with the memory 507, the communication module 503 and/or any other component, for example, through a bus. One or a plurality of input/output modules and/or other components may be included in the controller component 500.

Figure 6:
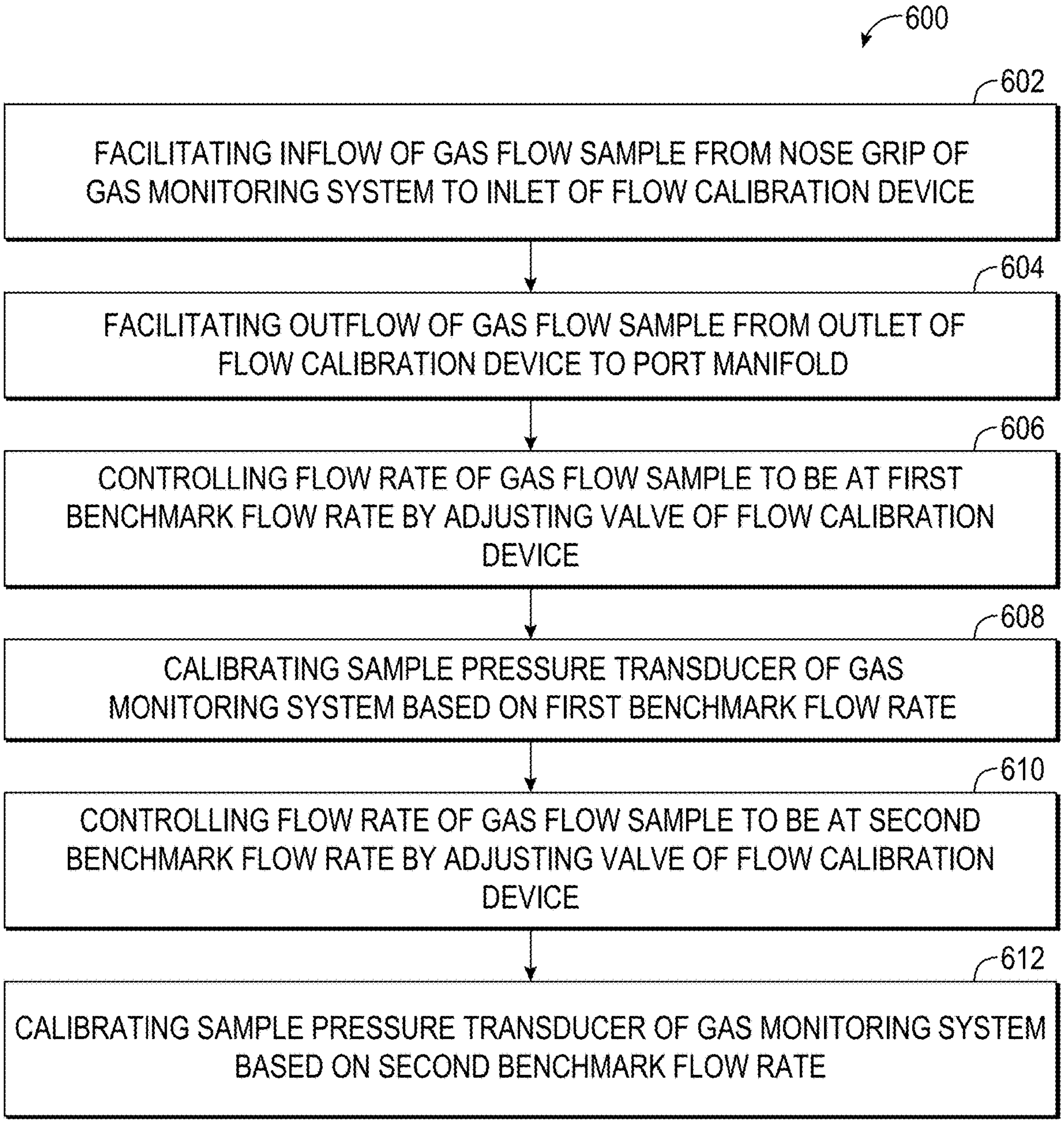
FIG. 6 illustrates an exemplary flow diagram depicting an exemplary method for calibrating a gas monitoring system, in accordance with various embodiments of the present disclosure.

Referring now to FIG. 6, an exemplary flow diagram illustrating an exemplary method for calibrating a gas monitoring system by a controller component in accordance with some exemplary embodiments of the present disclosure are provided. It is noted that each block of a flowchart, and combinations of blocks in the flowchart, may be implemented by various means such as hardware, firmware, circuitry and/or other devices associated with execution of software including one or more computer program instructions. For example, one or more of the steps/operations described in FIG. 6 may be embodied by computer program instructions, which may be stored by a non-transitory memory of an apparatus employing an embodiment of the present disclosure and executed by a processor component in an apparatus (such as, but not limited to, a controller component, a programable processor, a mobile device, a remote computing server, and/or the like). For example, these computer program instructions may direct the processor component to function in a particular manner, such that the instructions stored in the computer-readable storage memory produce an article of manufacture, the execution of which implements the function specified in the flowchart block(s).

As described above and as will be appreciated based on this disclosure, embodiments of the present disclosure may include various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

As shown in FIG. 6, an exemplary method 600 for calibrating a gas monitoring system in accordance with some exemplary embodiments described herein is illustrated. The exemplary method 600 may be executed by a computing device associated with a controller component (for example, the controller component 500 as illustrated and described above in connection with at least FIG. 5) including processing circuitry and memory (for example, the processing circuitry 501 and the memory 507 as illustrated and described above in connection with at least FIG. 5).

At step/operation 602, the controller component 500 may facilitate an inflow of a gas flow sample 402 from a nose grip 410 of the gas monitoring system 400 to an inlet 101 of a flow calibration device 100.

In some embodiments, as shown in FIG. 4, the nose grip 410 may comprise a by-pass mechanism (e.g., a Tee valve) that is configured to be mechanically engaged with the example flow calibration device 100 to facilitate the gas flow sample 402 to flow to the example flow calibration device 100 or with the port manifold 414 to facilitate the gas flow sample 402 to flow to the port manifold 414.

In some examples, the nose grip 410 may be mechanically engaged with the example flow calibration device 100, the gas flow sample 402 may flow through the example flow calibration device 100 to the port manifold 414, such that the example flow calibration device 100 may be used to perform a calibration process on the at least one sample pressure transducer 416 of the gas monitoring system 400.

In some examples, a calibration card may be inserted between the optical block 408 and the nose grip 410 to replace the media 406 during the calibration process.

At step/operation 604, the controller component 500 may facilitate an outflow of the gas flow sample 402 from an outlet 102 of the flow calibration device 100 to a port manifold 414 of the gas monitoring system 400.

In some embodiments, as shown in FIG. 1, a flow channel 103 may be defined between the inlet 101 and the outlet 102. In some examples, the inflow 110 of the gas flow sample 402 may pass through the flow channel 103 and exit the flow calibration device 100 via the outlet 102 to facilitate the outflow 111 of the gas flow sample 402.

In some embodiments, as shown in FIG. 4, the outlet 102 may be configured to engage with the port manifold 414, such that the gas flow sample 402 may be directed back to the gas monitoring system 400.

At step/operation 606, the controller component 500 may control a flow rate of the gas flow sample 402 to be at a first benchmark flow rate by adjusting a valve 106 of the flow calibration device 100.

In some embodiments, the valve 106 may be a needle valve configured to adjust the flow rate of the gas flow sample 402 in the flow channel 103. For example, as shown in FIG. 1, the valve 106 may include a controlling element **106*a* to adjust the flow rate of the gas flow sample 402 in the flow channel 103. For example, the controlling element 106*a* may be a turning knob, which controls a passageway (not shown) of the valve 106 by adjust the position of a needle 106*b*, such that the flow rate of the gas flow sample 402 in the flow channel 103** may be precisely controlled.

In some embodiments, the pressure transducer 105 may be electrically connected and/or coupled with the controller component 412 and the controller component 412 may be configured to determine the flow rate of the gas flow sample 402 according to the pressure transducer 105.

For example, the flow rate of the gas flow sample 402 may be controlled to be a first benchmark flow rate by adjusting the valve 106. For example, the first benchmark flow rate may be 200 cc/min.

At step/operation 608, the controller component 500 may calibrate at least one sample pressure transducer 416 of the gas monitoring system 400 based on the first benchmark flow rate.

In some embodiments, the controller component 412 may determine a first test flow rate based on the at least one sample pressure transducer 416 of the gas monitoring system 400. For example, if a magnitude of the first test flow rate is higher or lower than a magnitude of the first benchmark flow rate, the at least one sample pressure transducer 416 of the gas monitoring system 400 may be calibrated, such that the magnitude of the first test flow rate may equal to the magnitude of the first benchmark flow rate.

At step/operation 610, the controller component 500 may controlling the flow rate of the gas flow sample 402 to be at a second benchmark flow rate by adjusting the valve 106 of the flow calibration device 100.

For example, the flow rate of the gas flow sample 402 may be controlled to be a second benchmark flow rate by adjusting the valve 106. For example, the first benchmark flow rate may be 0 cc/min.

At step/operation 612, the controller component 500 may calibrate the at least one sample pressure transducer 416 of the gas monitoring system 400 based on the second benchmark flow rate.

For example, the controller component 412 may determine a second test flow rate based on the at least one sample pressure transducer 416 of the gas monitoring system 400. For example, if a magnitude of the second test flow rate is higher or lower than a magnitude of the second benchmark flow rate, the at least one sample pressure transducer 416 of the gas monitoring system 400 may be calibrated, such that the magnitude of the second test flow rate may equal to the magnitude of the second benchmark flow rate.

As described above and as will be appreciated based on this disclosure, embodiments of the present disclosure may include various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

What is claimed is:

1. A flow calibration device for a gas monitoring system, comprising:

an inlet configured to facilitate an inflow of a gas flow sample from a nose grip of the gas monitoring system;

an outlet configured to facilitate an outflow of the gas flow sample to a port manifold of the gas monitoring system;

a flow channel defined between the inlet and the outlet;

a pressure transducer, configured to calibrate at least one sample pressure transducer of the gas monitoring system; and a valve positioned between the inlet and the outlet, configured to adjust a flow rate of the gas flow sample between a first benchmark flow rate and a second benchmark flow rate.

2. The flow calibration device according to claim 1, wherein:

the valve is a needle valve configured to adjust the flow rate of the gas flow sample.

3. The flow calibration device according to claim 1, further comprising:

a resistor inserted in the flow channel to restrict the flow rate of the gas flow sample.

4. The flow calibration device according to claim 3, further comprising:

a first terminal positioned upstream of the resistor and a second terminal positioned downstream of the resistor, and the pressure transducer is configured to measure the flow rate of the gas flow sample by monitoring a pressure difference across the first terminal and the second terminal.

5. The flow calibration device according to claim 1, wherein:

the nose grip comprises a by-pass mechanism configured to divert the gas flow sample from the gas monitoring system to the inlet of the flow calibration device, and the inlet is configured to facilitate the inflow of the gas flow sample from the nose grip of the gas monitoring system.

6. The flow calibration device according to claim 5, wherein:

the by-pass mechanism is a Tee valve.

7. The flow calibration device according to claim 1, wherein:

the outlet is configured to facilitate the outflow of the gas flow sample to the port manifold of the gas monitoring system.

8. The flow calibration device according to claim 1, wherein:

the at least one sample pressure transducer is configured to measure the flow rate of the gas flow sample.

9. The flow calibration device according to claim 8, wherein:

the pressure transducer is configured to measure the flow rate of the gas flow sample.

10. The flow calibration device according to claim 9, wherein calibrating the at least one sample pressure transducer comprising:

controlling the flow rate of the gas flow sample to be at the first benchmark flow rate by adjusting the valve;

calibrating the at least one sample pressure transducer based on the first benchmark flow rate;

controlling the flow rate of the gas flow sample to be at the second benchmark flow rate by adjusting the valve; and calibrating the at least one sample pressure transducer based on the second benchmark flow rate.

11. The flow calibration device according to claim 10, wherein:

the first benchmark flow rate is 200 cc/min, and the second benchmark flow rate is 0 cc/min.

12. The flow calibration device according to claim 1, wherein:

the gas monitoring system further comprises an optical block and a media positioned between the optical block and the nose grip, and the optical block is configured to collect data by sensing a change in the media that is exposed to the gas flow sample.

13. The flow calibration device according to claim 12, wherein:

the gas monitoring system further comprises a controller component electrically coupled to the optical block, configured to determine a concentration of the gas flow sample based on the data collected on the optical block.

14. The flow calibration device according to claim 12, wherein:

the media is a chemcassette tape that changes color in an instance in which the chemcassette is exposed to the gas flow sample.

15. A method for calibrating a gas monitoring system by a controller component, comprising:

facilitating an inflow of a gas flow sample from a nose grip of the gas monitoring system to an inlet of a flow calibration device;

facilitating an outflow of the gas flow sample from an outlet of the flow calibration device to a port manifold of the gas monitoring system;

controlling a flow rate of the gas flow sample to be at a first benchmark flow rate by adjusting a valve of the flow calibration device;

calibrating at least one sample pressure transducer of the gas monitoring system based on the first benchmark flow rate;

controlling the flow rate of the gas flow sample to be at a second benchmark flow rate by adjusting the valve of the flow calibration device; and calibrating the at least one sample pressure transducer of the gas monitoring system based on the second benchmark flow rate.

16. The method according to claim 15, wherein:

the flow calibration device further comprises a flow channel defined between the inlet and the outlet, and the valve is positioned between the inlet and the outlet, configured to adjust the flow rate of the gas flow sample.

17. The method according to claim 16, wherein:

the flow calibration device further comprises a resistor inserted in the flow channel to restrict the flow rate of the gas flow sample.

18. The method according to claim 17, wherein:

the flow calibration device further comprises a first terminal positioned upstream of the resistor and a second terminal positioned downstream of the resistor, and the pressure transducer is configured to measure the flow rate of the gas flow sample by monitoring a pressure difference across the first terminal and the second terminal.

19. The method according to claim 15, wherein:

the nose grip comprises a by-pass mechanism configured to divert the gas flow sample from the gas monitoring system to the inlet of the flow calibration device, and the inlet is configured to facilitate the inflow of the gas flow sample from the nose grip of the gas monitoring system.

20. The method according to claim 15, wherein:

the first benchmark flow rate is 200 cc/m, and the second benchmark flow rate is 0 cc/m.

* * * * *